(12) United States Patent
Sirimanne (10) Patent No.: US 6,488,662 B2
(45) Date of Patent: Dec. 3, 2002

(54) PERCUTANEOUS CATHETER ASSEMBLY

(76) Inventor: Laksen Sirimanne, 2800 Keller Dr. #124, Tustin, CA (US) 92782

( * ) Notice: Subject to any disclaimer, the term of this patent is extended or adjusted under 35 U.S.C. 154(b) by 6 days.

(21) Appl. No.: 09/741,695

(22) Filed: Dec. 19, 2000

(65) Prior Publication Data

US 2002/0077600 A1 Jun. 20, 2002

(51) Int. Cl.$^7$ .............................................. A61M 5/178
(52) U.S. Cl. .............................. 604/164.01; 604/164.1
(58) Field of Search ........................ 604/164.1, 164.01, 604/164.04, 164.06, 164.09, 167.01, 167.02, 167.03, 167.04, 523, 533, 535, 198

(56) References Cited

U.S. PATENT DOCUMENTS

| | | | | |
|---|---|---|---|---|
| 4,000,739 | A | * | 1/1977 | Stevens .................... 128/214.4 |
| 4,411,655 | A | | 10/1983 | Schreck ...................... 604/165 |
| 4,798,591 | A | | 1/1989 | Okada ......................... 604/164 |
| 4,857,062 | A | * | 8/1989 | Russell ........................ 604/256 |
| 4,995,865 | A | | 2/1991 | Gahara et al. ................. 604/43 |
| 5,066,285 | A | | 11/1991 | Hillstead ..................... 604/164 |
| 5,114,408 | A | * | 5/1992 | Fleischhaker et al. ...... 604/167 |
| 5,250,036 | A | | 10/1993 | Farivar ....................... 604/164 |
| 5,279,551 | A | | 1/1994 | James .......................... 604/44 |
| 5,336,205 | A | | 8/1994 | Zenzen et al. .............. 604/280 |
| 5,405,329 | A | | 4/1995 | Durand ....................... 604/164 |
| 5,417,705 | A | | 5/1995 | Haber et al. ................ 606/185 |
| 5,505,710 | A | | 4/1996 | Dorsey, III .................. 604/158 |
| 5,649,911 | A | | 7/1997 | Trerotola ..................... 604/164 |
| 5,672,158 | A | * | 9/1997 | Okada et al. ................ 604/164 |
| 6,200,260 | B1 | * | 3/2001 | Bolling ........................ 600/16 |
| 6,228,052 | B1 | * | 5/2001 | Pohndorf ................... 604/96.01 |
| 6,245,045 | B1 | * | 6/2001 | Stratienko .............. 604/164.13 |

FOREIGN PATENT DOCUMENTS

| | | |
|---|---|---|
| DE | 91 11 200 U | 11/1991 |
| EP | 0 411 605 A1 | 2/1991 |
| EP | 0 411 605 A1 * | 6/1991 |
| WO | WO 99/16498 * | 4/1999 |
| WO | WO 99/21605 | 5/1999 |

OTHER PUBLICATIONS

PCT International Search Report, App. No.: PCT/US 01/42773, App. Date: Oct. 15, 2001.

* cited by examiner

Primary Examiner—Charles G. Freay
Assistant Examiner—Han L. Liu
(74) Attorney, Agent, or Firm—Knobbe, Martens, Olson & Bear LLP (57) ABSTRACT

The present invention is a percutaneous catheter assembly intended for long-term blood flow of several days, said assembly comprising generally three components: a catheter housing having three sections, each of preferably differing diameter, with a set of perforations in a distal section, an end cap for closing off a proximal end of the catheter housing during insertion, and a dilator having an outer diameter substantially the same size as the inner diameter of the smallest section of the catheter housing, the dilator being configured to pass radiopaque contrast through a first and second set of openings in the dilator and the perforations in the catheter housing. The present invention further comprises a method of percutaneous blood perfusion in which the catheter assembly is used without the need for an introducer sheath.

17 Claims, 3 Drawing Sheets

PERCUTANEOUS CATHETER ASSEMBLY

FIELD OF THE INVENTION

The present invention relates generally to a percutaneous catheter for the introduction and withdrawal of fluids from the vascular system of a patient and, more particularly, to a catheter assembly that employs a multi-diameter catheter housing, a proximal end cap for the housing having a central bore therein, and a dilator for passage through the catheter housing and the cap.

BACKGROUND OF THE INVENTION

Under various circumstances in the treatment of a patient experiencing cardiac problems, it is desired to cannulate the patient's vasculature for either blood perfusion or other treatment, such as the insertion of a catheter, a cannulae or an IABP. In a surgical environment, the surgeon typically exposes the blood vessel through a cut-down process. To cannulate the blood vessel, a small slit is made in the vessel wall of a clamped vessel to permit insertion of either an arterial perfusion catheter or a therapeutic catheter for the application of, for example, an IABP. With a perfusion catheter, often an atraumatic tip dilator is positioned concentrically within the catheter over a guidewire to assist in advancing the catheter to the desired point with minimal trauma to the epithelial layer. The dilator and guidewire are then removed and the catheter left in place for treatment.

In an environment such as a cardiac catheterization laboratory, an interventional clinician is not trained to perform a surgical cut down to penetrate the patient's vasculature. Thus, a percutaneous cannulation is necessary. With a percutaneous cannulation, a very small diameter insertion needle having a hollow lumen therein is used to penetrate the vessel wall. Then a guidewire is inserted through the insertion needle, and the needle removed. Next, an angio-cath, which may be made of polyethylene, is inserted over the guidewire, replacing the needle. Where it is desired only to establish a low flow rate of fluid percutaneously, either for aspiration or infusion, the angio-cath is left in place. The angio-cath may then be connected at its proximal end to a source of fluid or a syringe to inject fluid or to remove blood.

Where it is desired to establish a larger flow of fluid or to apply some level of cardiac treatment to the patient, a guide wire may then be inserted within the lumen of the insertion needle to permit removal of the insertion needle, leaving the guide wire in place. Once the guide wire is positioned where desired, an introducer sheath is inserted over the guide wire and through the vessel wall. In order to dilate the wall opening with minimal trauma to the blood vessel, a stylet (dilator) is placed concentrically within the introducer sheath so that both ride over the guide wire to position the sheath within the vessel wall. The dilator has a very small distal diameter to permit easy penetration through the small opening in the vessel wall. The dilator is tapered with increasing diameter toward the proximal end up to the diameter of the sheath so that the opening in the vessel wall is gradually expanded. Once the sheath is positioned within the vessel wall, the dilator is then removed, leaving the sheath within the wall with the guide wire remaining therethrough. The clinician has now established communication with the blood vessel at the desired diameter. The guide wire is then typically advanced into the patient's vasculature as far as is desired to either establish remote fluid communication with the patient or to a point where treatment with an perfusion catheter or other device is desired. For the passage of large devices or for the passage of a large volume of blood, a large diameter introducer sheath is required. With this sheath/guide wire arrangement, the clinician may exchange any one of a number of catheters without risk of losing that communication, because the sheath remains in place. The clinician threads the catheter over the guide wire to the desired location. Even where treatment is discontinued, the sheath may be left in place temporarily to permit the clinician to apply treatment again without having to reopen the blood vessel wall. Typically, the introducer sheath has a hemostasis valve at its proximal end to control the flow of fluid therethrough.

Once the sheath is in place, a perfusion catheter of a desired size (smaller than the sheath, however) may be inserted over the guide wire and through the sheath. The guide wire may then be removed, if so desired. Where fluid communication with the patient is desired at a location remote from the penetration site, a guiding catheter may first be inserted within the sheath and over the guide wire while it is advanced to the desired point in the patient's vasculature. To serve its function as a guide, the guiding catheter typically has a radiopaque marker at the distal end that may be seen through an x-ray monitor via fluoroscopy technique. The marker typically consists of a metallic ring detectable via fluoroscopy by the x-ray. With such a marker, the clinician may follow the location of the distal end as it advances through the vasculature. If desired, radiopaque contrast fluid may be directed through the guiding catheter and out into the vessel at the distal end to permit viewing of the vasculature through which the guiding catheter is passing. This serves the purpose of showing the general profile of the vessel as the guiding catheter is advanced. Such contrast may expose problems with continuing to proceed in that particular vessel before the guiding catheter has advanced too far.

Once the guiding catheter has been advanced to the desired point, an intravascular device, such as an angioplasty balloon, may be inserted the guiding catheter for vascular treatment. Or, a perfusion catheter may be inserted within the guiding catheter as well, to permit blood flow. In either case, it may be desirable to remove both the guiding catheter and the guide wire to permit treatment to be applied. The introducer sheath may be of the type that remains in place, or it may be of the type that tears away, leaving whatever device is in the sheath to maintain the opening in the vessel wall. Once the sheath is removed, however, that device (i.e., a guiding catheter or other device) provides the only vehicle to maintain the vessel wall opening at that diameter.

The advantage of an introducer sheath is that it permits exchange of catheters over time without losing the benefit of an established vessel wall opening. The disadvantage is that it hampers the use of large diameter catheters, i.e., where it is desired to establish fluid communication with the patient's vasculature at high flow rates. With a large diameter introducer sheath, occlusion of the blood vessel may occur, leading to possible ischemia of the limb served by the blood vessel. For example, if it is desired to establish fluid communication on the order of 1.5 liters per minute or greater through the femoral artery, it would be desirable to use a 12 French (outer diameter) perfusion catheter. To do so, however, would require at least a 12 French (inner diameter) introducer sheath. An even larger sheath would be necessary if it were also desired to have a guiding catheter inserted within the sheath and the perfusion catheter inserted within the guiding catheter. Given the size of the femoral artery, such a large introducer sheath has risks of occluding the femoral artery.

Thus, it would be desirable to establish a large fluid flow connection percutaneously to an artery or vein without the need for an introducer sheath or without a guiding catheter, but yet still provide a way of serving the function normally served by a guiding catheter.

SUMMARY OF THE INVENTION

It is therefore an object of the present invention to establish a large fluid flow connection percutaneously to an artery or vein without either an introducer sheath or a guiding catheter. In that regard the present invention comprises a percutaneous catheter assembly intended for long-term use of several days. The catheter assembly comprises generally three components: a catheter housing having three sections, each of preferably differing diameter, an end cap for closing off the proximal end of the catheter housing during insertion, and a dilator having an outer diameter substantially the same size as the inner diameter of the smallest section of the catheter housing.

The catheter housing of a preferred embodiment comprises three sections, a distal end section, which is tapered at the tip to facilitate penetration of a vessel wall, a mid-section having an inner diameter greater than the distal section, having a tapered transition between the distal end section and the mid-section, and a proximal section having an inner diameter of preferably about ⅜" to permit connection to standard components, such as a flow probe and/or a pump. A polyester sleeve may be provided over the catheter housing, positioned to correspond with the point on the catheter adjacent the patient's skin. The sleeve may be sutured to the patient to resist relative movement. In addition to or in place of the sleeve, a disk surrounding the catheter housing may be used at or about the same position on the catheter. Also, a reinforcing member, such as a helical coil, is provided in the wall of at least the distal end section and the mid-section of the catheter for reinforcement purposes. At the distal end of the catheter housing, one or more radiopaque markers may be positioned to assist in intravascular location during insertion of the catheter assembly. Proximate the distal tip is a plurality of openings or perforations.

Various coatings may be applied to the catheter housing to improve its performance. For example, an anti-bacterial or anti-microbial coating may be applied to reduce infection risk; an anti-thrombotic coating may be applied to reduce adhesions to the catheter housing and any other component that comes into contact with blood for any significant period of time.

The cap is configured to seal off the proximal end of the catheter housing during insertion until the proximal end of the catheter housing is ready for connection to a tube for aspiration or infusion. The cap includes an internal bore that has an inner diameter the same size as the dilator.

The dilator comprises a long tube with a concentrically tapered distal end and a hemostasis valve at the proximal end. Extending from the hemostasis valve is a tube with a luer connector for connecting to a source of radiopaque contrast. The dilator includes a plurality of struts extending axially through the length of the dilator for stiffening the dilator. The distal tip of the dilator includes a plurality of openings, a first set positioned preferably adjacent the tip and a second set proximal thereto. It is intended that, when the dilator is placed within the catheter housing, that the distal tip of the dilator project beyond the distal tip of the housing so that the second set of holes in the dilator align generally with the perforations in the distal end of the catheter housing.

The invention also comprises a preferred method of operation of the catheter assembly. The method comprises penetrating a patient's vasculature so as to permit a guide wire to be inserted in the patient's blood vessel. The cap is placed within the proximal end of the catheter housing. The dilator is then placed within the catheter housing through the cap so that the distal tip of the dilator extends just beyond the distal tip of the catheter housing. Saline is flushed through the hemostasis valve and out through the distal tip to flush the assembly of air. The catheter assembly is then placed over the guide wire and inserted through the patient and into the blood vessel. Radiopaque contrast may then be injected through the hemostasis valve and out through the first set of holes in the distal end of the dilator to permit detection of the distal end as the catheter assembly is being advanced through the patient. The radiopaque contrast also advantageously exits the second set of holes in the distal end of the catheter so as to detect the location of the perforations in the catheter housing.

Once the catheter assembly is advanced to the desired point within the blood vessel, the guide wire may be removed. Then the dilator may then be removed, leaving the cap in place. When the distal tip of the dilator is within the proximal section of the catheter housing, a hemostat may be used to clamp the catheter so as to prevent the flow of blood out of the proximal end of the catheter housing. Also, once the catheter housing is positioned, a sleeve and/or disk may be used to secure the catheter housing to the patient to minimize relative movement between the patient and the catheter housing. At that point, the cap may be removed and a delivery (or withdrawal) line attached to the proximal end of the catheter housing.

DETAILED DESCRIPTION OF THE PREFERRED EMBODIMENT

Figure 1:
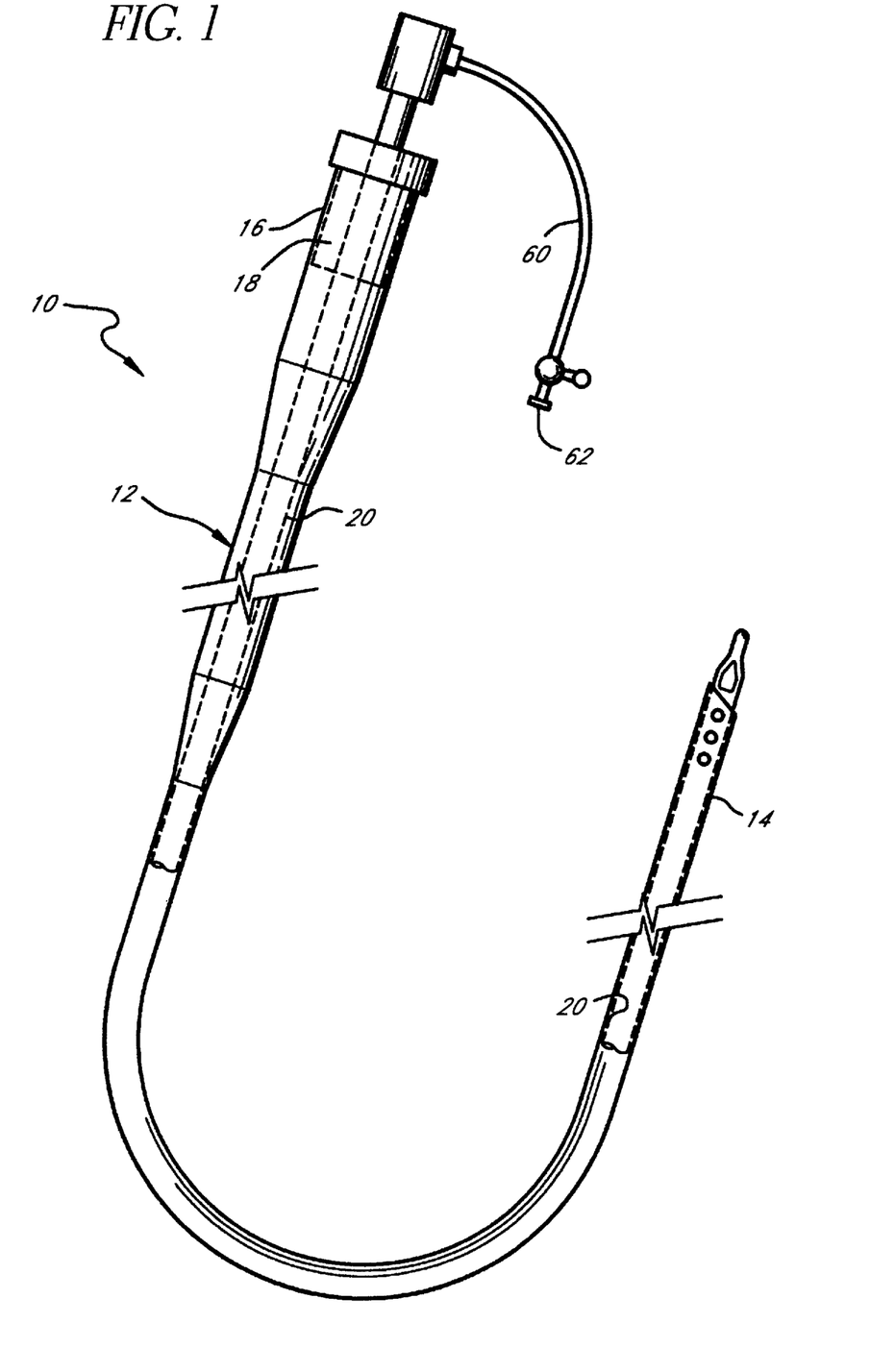
FIG. 1 is a perspective view of the present invention percutaneous catheter assembly showing its preferred components in an assembled position.

Reference is now made to the figures wherein like parts are designated with like numerals throughout. Referring first to FIG. 1, the present invention comprises a percutaneous catheter assembly 10 that may be used for long-term use of at least several days. FIG. 1 shows the three main components of the assembly 10 in assembled form for application to a patient. The assembly 10 comprises a catheter housing 12 having a single lumen therein, wherein the housing 12 has a distal end 14 and a proximal end 16, with the distal end 14 intended to project into the vascular system of a patient. The assembly 10 further comprises an end cap 18 configured to fit snugly within the proximal end of the catheter housing 12 to seal the housing against flow through the proximal end during use. The assembly 10 also comprises a dilator 20 configured to protrude through the end cap 18 and through the lumen of the catheter housing 12.

Figures 2, 3:
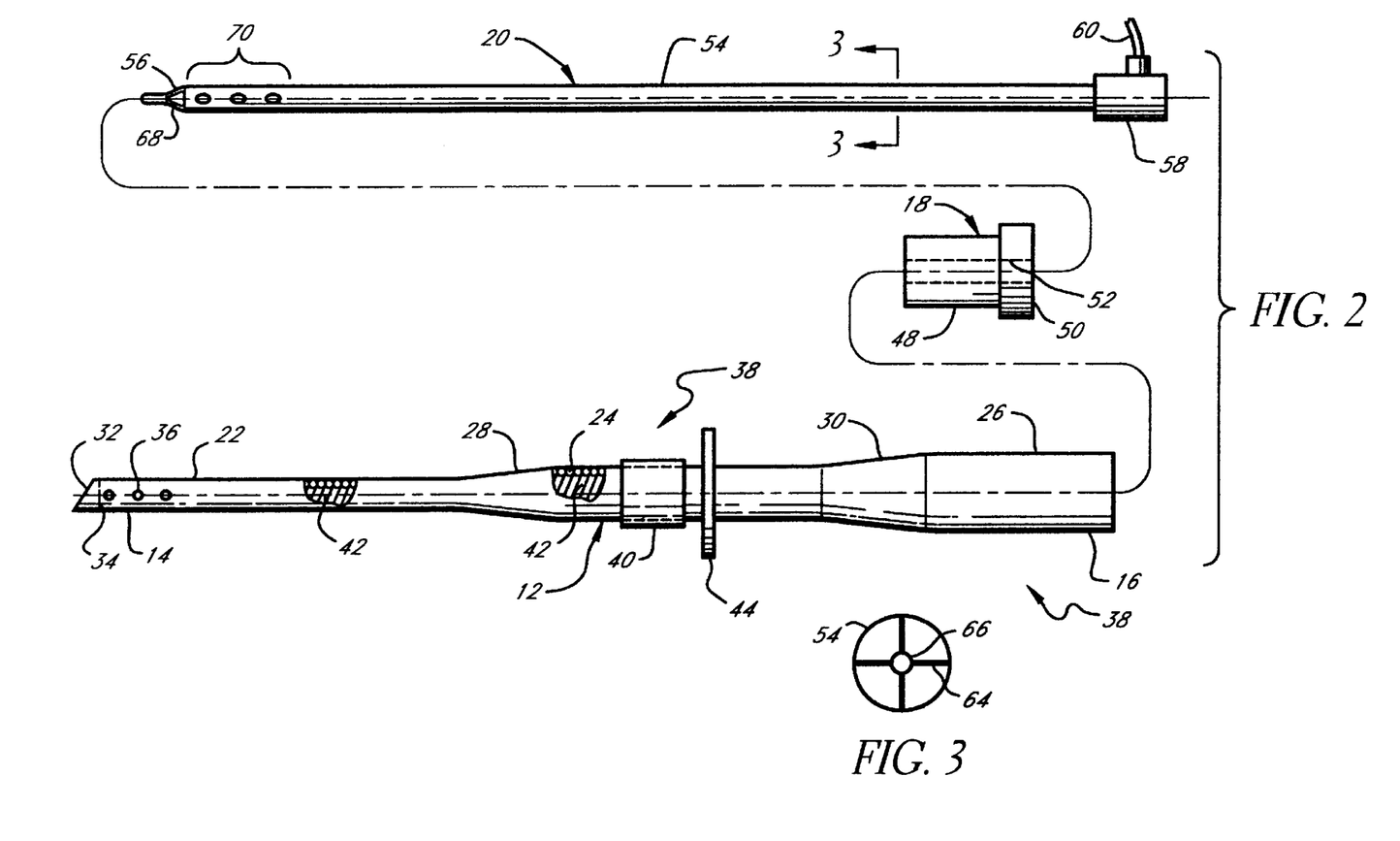
FIG. 2 is a side view of the catheter housing, the end cap, and the dilator of the assembly of FIG. 1.
FIG. 3 is a cross-sectional view of the dilator of FIG. 2.
Figure 4:
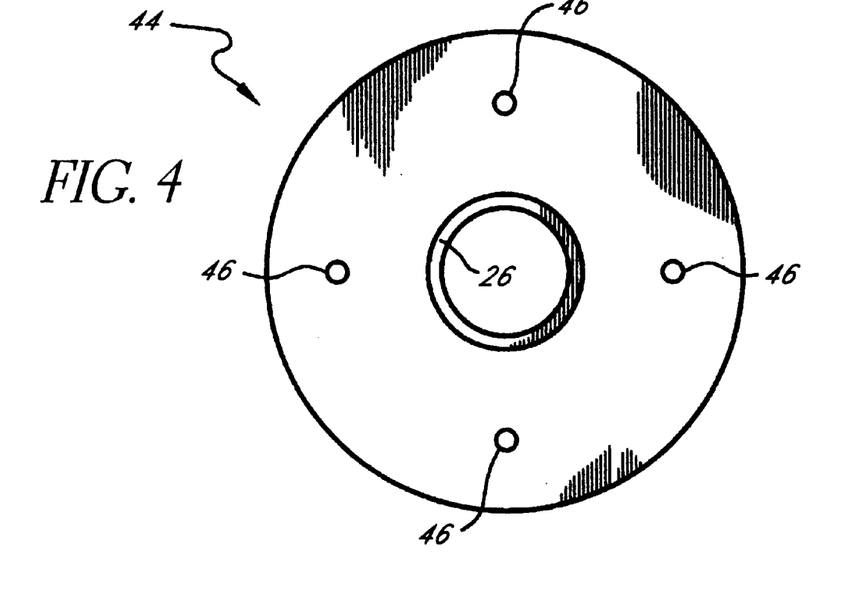
FIG. 4 is a front view of the suturing disk applied to the catheter housing.
Figures 5, 6:
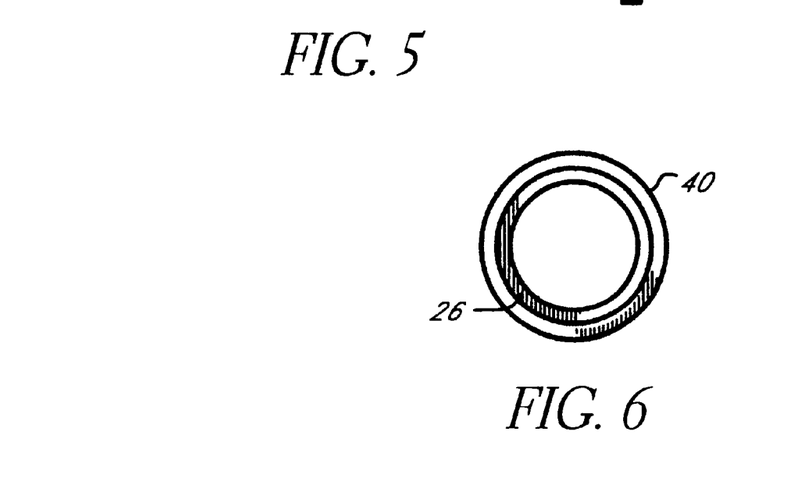
FIG. 5 is a side view of the sleeve applied to the catheter housing with internal structure shown in broken lines.
FIG. 6 is a front view of the sleeve applied to the catheter housing.

Referring to FIG. 2, the catheter housing 12 can be described in greater detail. The catheter housing is made of a pliable but durable plastic material, such as urethane, although other similar materials would be acceptable. The catheter housing 12 preferably has three sections: a distal section 22, a mid-section 24, and a proximal section 26, each of different diameters. The distal section 22 has a relatively small inner diameter of preferably about 10 French, although other sizes that would effectively pass through a blood vessel without patient trauma while permitting high blood flow would be acceptable. The mid-section 24 has an inner diameter of preferably about 16 French, with a first tapered section 28 positioned between the distal section 22 and the mid-section 24. The mid-section is of larger diameter than the distal section to prevent kinking of the catheter during insertion and tunneling. Sizes other than 16 French would be acceptable. The proximal section 26 has an inner diameter of preferably ⅜" to permit connection to standard components, such as a flow probe or a pump. The proximal section 26 is preferably configured to slip onto a barbed connector, although other connector configurations would be acceptable. A second tapered section 30 is positioned between the mid-section 24 and the proximal section 26. It is intended that only the distal section 22 would penetrate the patient's vascular system, with the mid-section sized to permit subcutaneous tunneling. The length of the distal section 22 may be selected depending upon where the vessel penetration site is and where in the patient's vasculature (remote from the site) the clinician desires to establish fluid communication. For example, if the vessel penetration site were somewhere on the left femoral artery, but the fluid communication site were further up in the descending aorta, the distal section 22 would need to be sufficiently long to span that distance. Similarly, the length of the mid-section 24 may be selected depending upon where the vessel penetration site is and where the desired patient exit site is. For example, if it were desired to penetrate the left axillary artery but have the patient exit site close to the patient's waist, the mid-section 24 would need to be sufficiently long to span that distance. Also, the thickness of the proximal section 26 is preferably configured to permit the attachment of an external sonic based flow meter thereto.

A tip 32 of the distal section 22 is preferably tapered to facilitate penetration of a vessel wall, although it not need be tapered if so desired. Adjacent the distal section tip 32 is a radiopaque marker 34 to assist in locating the tip of the catheter housing 12 during insertion. Proximate the distal tip 32 is a first set of openings comprising one or more perforations 36 in the wall of the catheter housing that serve to permit peripheral distribution of a contrast fluid, i.e., radiopaque contrast, from the distal section 22 of the catheter housing 12 during insertion, as explained further below. As described further below, that peripheral distribution serves to better facilitate location and insertion of the distal end of the catheter housing 12. Other arrangements of one or more perforations would be acceptable.

Referring to FIGS. 1, 2, 5 and 6, the preferred embodiment of the catheter assembly 10 further comprises an interface portion 38 that comprises a sleeve 40 comprising a synthetic material for permitting enhanced securement of the catheter assembly 10 to a patient during use. During use, particularly when the patient is ambulatory, there is a tendency for a percutaneously applied catheter to move relative to the patient as the catheter slides at the exit site. Having a sleeve with a configuration and characteristic that permits a physician to suture the catheter to the patient would be a significant advantage. Preferably, the sleeve 40 comprises a third synthetic material having a textile property to enhance the use of sutures as a means for securing the catheter to the patient. More preferably, the sleeve 40 is made of polyester or other material having similar properties. The sleeve 40 is bonded to the catheter assembly 10 in a manner to prevent relative movement between the sleeve and the catheter. The length of the sleeve 40 may be selected as desired. The length should be sufficient, however, to give some flexibility to the physician in the placement of the catheter with respect to the exit site. In one embodiment, the sleeve 40 is manufactured already bonded to the catheter with a length pre-selected to give flexibility to the physician. If desired, the sleeve length may be kept at a minimum but be manufactured discretely from the balance of the catheter, permitting, if desired, the physician to locate the sleeve where desired and then to bond the sleeve to the catheter after it is optimally positioned on the catheter. For short term use, a technique as simple as clamping the extracorporeal portion of the sleeve to the catheter wall without occluding the inner flow path might be acceptable. For longer term use, bonding with an adhesive at the proximal end of the sleeve with a bonding material that would not travel undesirably toward the skin and into the patient would be desired.

Referring now to FIG. 1, a preferred embodiment of the catheter housing 12 preferably further comprises axial reinforcing member 42 preferably extending the entire length of the distal end section and, if desired, the mid-section, for purposes of adding stiffness to the catheter housing 12. The reinforcing member 42 may be a helical coil, as is known in the art. It need not be limited to helical coils, however, as many other reinforcement members are known in the art. For example, the axial reinforcing member 42 need not extend the entire length of the catheter housing 12. Where the catheter housing material is sufficiently stiff, however, the axial reinforcing member 42 may not be necessary so long as the catheter housing 12 is sufficiently stiff to withstand axial forces applied at its proximal end to facilitate insertion into the patient's vascular system.

As shown in FIG. 1, the catheter housing 12 may also include a positioning disk 44. In one embodiment, the disk is integrally made with the catheter housing so that relative movement between the disk and catheter housing is minimized. In another embodiment, the disk 44 and catheter housing 12 are separately made and the disk 44 has an inner diameter which is sufficiently larger than the outer diameter of the portion of the catheter housing exiting the patient's skin to permit relative movement of the disk over the housing. This relative movement permits the physician to locate the disk where desired. Once positioned, the disk is fixed to the catheter housing, minimizing relative movement between the catheter housing and the disk. In one embodiment, the disk is fixed by a tight interference fit. In yet another embodiment the physician bonds the disk to the catheter after it is optimally positioned on the catheter. For short term use, a technique as simple as clamping the disk to the catheter wall without occluding the inner flow path might be acceptable. For longer term use, bonding with an adhesive at the proximal end of the disk with a bonding material that would not travel undesirably toward the skin and into the patient would be desired. The disk 44 may also have suturing features 46 which are conveniently placed around the disk to facilitate securement of the disk 44—and hence the catheter housing 12—to the patient's body. As mentioned above, in connection with the sleeve 40, this may prevent relative movement of the percutaneously inserted catheter housing.

The cap 18 is configured to seal off the proximal end of the catheter housing during insertion until the proximal end of the catheter housing is ready for connection to a tube or other device for aspiration or infusion. The cap 18 has a first section 48 having an outer diameter the same size as the inner diameter of the proximal end 30 of the catheter housing 12 to permit a tight but removable fit therebetween. The cap 18 also has a second section 50 configured to enclose the end of the proximal section 26 of the catheter housing when the cap 18 is fully inserted, as shown in FIG. 1. Traversing axially the entire length of the cap 18 is a central bore 52 having an inner diameter preferably the same or just slightly larger than the outer diameter of the dilator 20. The cap 18 is configured to permit the dilator 20 to slide through the cap 18 while the cap is inserted into the proximal end of the catheter housing. The inner diameter of the cap 18 may also be configured with ridges or teeth which further grip the dilator to provide both a snug fit and also improve the seal. This may prevent blood from seeping out at the interface between the dilator 20 and the cap 18 at the proximal end of the cap. The end cap may be made of a polymer such as rubber, polypropylene or silicone, but may comprise other similar materials as well.

The dilator 20 generally comprises a long tube 54 with a lumen therethrough having a concentrically tapered open distal end 56 and a hemostasis valve 58 at the proximal end. The outer diameter of the tube 54 is preferably smaller than 10 French so that there is clearance fit between the distal end 56 of the tube 54 and the distal section 22 of the catheter housing. Extending from the hemostasis valve 58 is a tube 60 having a luer connector 62 (FIG. 1) at the end for connecting to a source of radiopaque contrast (not shown). Referring to FIG. 3, the dilator 20 preferably further comprises a plurality of struts 64 extending preferably the length of the dilator for purposes of adding stiffness to the tube 54. The struts 64 need not extend continuously along the length of the lumen of the dilator and preferably do not extend into the tapered distal end 56. The struts 64 converge radially inward toward a central axial hub 66. The central hub 66 has an inner diameter sufficiently large to permit passage therethrough of a guide wire, described more fully below. A hub diameter of at least 0.038 inches is preferable. The dilator with struts may be configured similar to off-the-shelf multi-lumen tubes presently available. The dilator is preferably made of a somewhat stiffer material than the catheter housing, preferably polyethylene, polypropylene, or other similar material. Where the material chosen is sufficiently stiff, struts may not be necessary. Either way, the dilator must be sufficiently stiff to withstand axial forces applied at its proximal end to facilitate insertion of the catheter housing and the dilator into and through a patient's vascular system.

The distal end 56 of the dilator 20 preferably comprises at least one opening 68 in a side wall of the dilator, but preferably a plurality of openings comprising a first set, preferably positioned close to the distal end 56 and more preferably on the tapered portion of the distal end so that at least one of the openings in the first set of openings, but preferably more than one, at least partially projects distally of the tip 32 of the catheter housing 12 when the dilator 20 is inserted within the housing, as shown in FIG. 1. The projection of the first set of openings 68 beyond the catheter housing permits ejection of the radiopaque contrast axially forward of the catheter housing 12 during the insertion process. Positioned proximally from the first set of openings 68 is at least one other opening or perforation 70, but preferably a plurality of openings comprising a second set positioned so that, when the dilator 20 is placed within the catheter housing 12, the second set of openings align generally axially and preferably radially with the perforations 36 in the distal section 22 of the catheter housing. The radiopaque contrast flowing outwardly through the second set of openings 70 will preferably pass directly into and through the first set of openings or perforations 36 in the catheter housing 12. When axially and radially aligned, the contrast in the lumen of the catheter housing 12 will pass through the openings 70 and directly out of the perforations 36 into the patient's blood vessel. When not aligned, the contrast will pass through the openings 70 and into the lumen of the catheter housing 12 before passing through the perforations 36. In either case, the contrast projects axially forward from the first set of openings 68 in the dilator.

Thrombosis is a common reaction when foreign matter is introduced into the vasculature. This can interfere with treatments involving insertion of foreign matter, such as catheters, into the vasculature by causing apertures and lumens to become occluded. This problem is especially acute in longer term treatments where significant build-up can occur due to the length of time the cannula is in the vessel. As a result, certain coatings can be beneficial if applied to cannulae inserted into the vasculature. For example, an anti-thrombotic coating is especially useful for longer term treatments because it prevents adhesion of blood components to the coated surface, which might otherwise eventually occlude a lumen or aperture. For this reason, at least the interior and exterior of the catheter housing 12 may have an anti-thrombotic coating. Also, if any other catheter housing component is exposed to the interior lumen of the catheter housing 12, it too may be coated.

Since patients using this improved percutaneous catheter assembly are ambulatory, there is an increased risk of infection at the patient's exit site. Consequently, anti-microbial or anti-bacterial coating may be beneficial, especially in relatively longer term treatments. When placed at least on the exterior surface of the catheter housing 12, this coating reduces the chance of infection occurring at or near the patient's exit site. Of course, any securing device used in connection with the catheter housing 12, such as the sleeve 40 or disk 44, may also advantageously use an anti-microbial or anti-bacterial coating to reduce the risk of infection of the patient's exit site.

The invention also comprises a method of operation of the catheter assembly 10. The method comprises penetrating the arterial site with a standard cannulation procedure, such as the Seldinger technique described in part above, so as to permit a guide wire to be inserted in the blood vessel (not shown). The cap 18 is placed within the proximal section 26 of the catheter housing 12. The dilator 20 is then placed within the catheter housing 12 through the cap 18 so that the distal end 56 of the dilator 20 extends beyond the distal tip 32 of the catheter housing. Saline is flushed through the hemostasis valve 58 and out through the distal end 56 to flush the catheter assembly 10 of any air that would be detrimental to a patient. The catheter assembly 10 is then placed over the guide wire and inserted through the patient and into the blood vessel. Radiopaque contrast is then injected through the hemostasis valve 58 and out through the first set of openings 68 in the distal end 56 of the dilator 20 to permit detection of the distal end 56 as the catheter assembly 10 is being advanced through the patient. The radiopaque contrast also exits the second set of holes 78 in the dilator 20 and the perforations 36 of the catheter housing 12 so as to permit detection of the location of the distal end 14 of the catheter housing.

Once the catheter assembly 10 is advanced to the desired point within the blood vessel, the guide wire is removed. Then the dilator 20 is retracted from the catheter housing 12, leaving the cap 18 in place. The cap 18 prevents backflow of the blood through the proximate end 16 of the housing 12 during removal of the dilator 20. When the distal end 56 of the dilator 20 is within the proximal section 26 of the catheter housing 12, a hemostat (not shown) may be used to clamp the catheter housing so as to prevent the flow of blood out of the proximal end 16 of the catheter housing. At that point, the cap 18 may be removed from the catheter housing 12 and a delivery line attached to the proximal end 16 of the catheter housing for aspiration or infusion.

The present invention has application to most any aspiration and infusion treatment desired. It has particularly beneficial application to the system and method described in U.S. Ser. No. 09/166,005, now U.S. Pat. No. 6,200,260 to Bolling, U.S. Ser. No. 09/289,231 to Bolling, Ser. No. 09/470,841 to Bolling et, al., now U.S. Pat. No. 6,387,037, and Ser. No. 09/552,979 to Bolling et al, now U.S. Pat. No. 6,390,969, each of which are incorporated in their entirety by reference.

In the case where the exit site of the patient is desired to be positioned away from the penetration site of the blood vessel, the present invention catheter assembly 10 is configured to permit the assembly 10 to be tunneled subcutaneously between the two sites. For example, if it were desired to have the catheter assembly connected to a delivery line exiting the patient at the waist area, but have the catheter penetrate the left axillary artery, the above procedure could be followed at the shoulder area of the patient to cannulate the blood vessel, and then follow a tunneling procedure to bring the proximal end of the catheter housing subcutaneously toward the patient's waist area while the distal end remains within the left axillary artery. For example, with the system described in Ser. No. 09/166,005 (U.S. Pat. No. 6,200,260), it may be desired to have the patient carry a subcardiac pump near the patient's waist area with the inflow and outflow lines penetrating the patient's skin proximate the pump. Where it is desired that the inflow line connect to the left femoral artery and the outflow line connect to the patient's left axillary artery, the above procedures could be followed. If a single penetration site were desired, a multi-lumen catheter system could be used to penetrate the patient's vascular system, as described in Ser. No. 09/470,841, now U.S. Pat. No. 6,387,037, but following the procedures t described above. In that regard, it is contemplated that the catheter housing of the present invention be configured to have more than one lumen therethrough for certain applications.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes that come within the meaning and range of equivalency of the claims are to be embraced within their scope.

What is claimed is:

1. A percutaneous catheter assembly comprising:
   a catheter housing having a distal end and a proximal end and a lumen therethrough, said distal end configured to penetrate a blood vessel wall and pass axially through the blood vessel without trauma to the patient, said proximal end configured to connect to a standard sized blood pump, said catheter housing having a transition section between the distal end and the proximal end, said catheter housing further comprising a catheter housing side wall having at least one perforation therein in fluid communication with said lumen to permit the passage of a contrast fluid through said perforation;
   a dilator having a distal end and a proximal end, said dilator configured to pass axially through the lumen of said catheter housing, said dilator having at least one opening in a side wall thereof proximate the distal end of the dilator for permitting passage of the contrast fluid therethrough, said proximal end of said dilator configured to receive said contrast fluid from an external source, said dilator configured with sufficient stiffness to withstand axial forces on said dilator during insertion of the dilator into the lumen of said catheter housing and during insertion of both said dilator and said catheter housing into the patient's vascular system; and
   an end cap having a central bore therethrough, said end cap configured to seal the proximal end of said catheter housing from fluid flow when said dilator is inserted within the lumen of said catheter housing while said cap is inserted within said proximal end of said catheter housing;
   wherein the dilator further comprises at least one additional opening in said dilator side wall, said side wall openings being axially positioned relative to each other such that one opening is positioned more distal than the other opening so that, when the dilator is inserted within said catheter housing, the more distal opening is positioned so that at least a part thereof projects distally beyond the distal end of the catheter housing and wherein the other opening is positioned so as to be generally radially aligned with the perforation of said catheter housing side wall.

2. A percutaneous catheter assembly comprising:
   a catheter housing having a distal end and a proximal end and a lumen therethrough, said distal end configured to penetrate a blood vessel wall and pass axially through the blood vessel without trauma to the patient, said proximal end configured to connect to a standard sized blood pump, said catheter housing having a transition section between the distal end and the proximal end, said catheter housing further comprising a catheter housing side wall having at least one perforation therein in fluid communication with said lumen to permit the passage of a contrast fluid through said perforation;
   a dilator having a distal end and a proximal end, said dilator configured to pass axially through the lumen of said catheter housing, said dilator having at least one opening in a side wall thereof proximate the distal end of the dilator for permitting passage of the contrast fluid therethrough, said proximal end of said dilator configured to receive said contrast fluid from an external source, said dilator configured with sufficient stiffness to withstand axial forces on said dilator during insertion of the dilator into the lumen of said catheter housing and during insertion of both said dilator and said catheter housing into the patient's vascular system; and
   an end cap having a central bore therethrough, said end cap configured to seal the proximal end of said catheter housing from fluid flow when said dilator is inserted within the lumen of said catheter housing while said cap is inserted within said proximal end of said catheter housing;
   wherein the catheter housing has a mid-section, a distal section, and a proximal section, the mid-section having a diameter greater than the diameter of the distal section but less than the diameter of the proximal section.

3. The catheter assembly of claim 2 further comprising a disk comprising a synthetic material having a suturing feature, said disk positioned at and surrounding a part of the proximal section of said catheter housing, said disk serving to provide a substrate upon which a treating physician may secure said catheter housing to the patient to minimized relative movement therebetween.

4. A percutaneous catheter assembly comprising:

a catheter housing having a distal end and a proximal end and a lumen therethrough, said distal end configured to penetrate a blood vessel wall and pass axially through the blood vessel without trauma to the patient, said proximal end configured to connect to a standard sized blood pump, said catheter housing having a transition section between the distal end and the proximal end, said catheter housing further comprising a catheter housing side wall having at least one perforation therein in fluid communication with said lumen to permit the passage of a contrast fluid through said perforation;

a dilator having a distal end and a proximal end, said dilator configured to pass axially through the lumen of said catheter housing, said dilator having at least one opening in a side wall thereof proximate the distal end of the dilator for permitting passage of the contrast fluid therethrough, said proximal end of said dilator configured to receive said contrast fluid from an external source, said dilator configured with sufficient stiffness to withstand axial forces on said dilator during insertion of the dilator into the lumen of said catheter housing and during insertion of both said dilator and said catheter housing into the patient's vascular system; and an end cap having a central bore therethrough, said end cap configured to seal the proximal end of said catheter housing from fluid flow when said dilator is inserted within the lumen of said catheter housing while said cap is inserted within said proximal end of said catheter housing;

wherein the dilator further comprises a lumen and struts axially positioned within the lumen of said dilator for stiffening the dilator, the distal end of said dilator having being tapered.

5. The assembly of claim 4 wherein the struts connect to a hub centrally positioned longitudinally in said dilator to permit the passage of a guide wire through said hub. lumen of said dilator for stiffening the dilator, the distal end of said dilator having being tapered.

6. A percutaneous catheter assembly comprising:

a catheter housing having a distal end and a proximal end and a lumen therethrough, said distal end configured to penetrate a blood vessel wall and pass axially through the blood vessel without trauma to the patient, said proximal end configured to connect to a standard sized blood pump, said catheter housing having a transition section between the distal end and the proximal end, said catheter housing further comprising a catheter housing side wall having at least one perforation therein in fluid communication with said lumen to permit the passage of a contrast fluid through said perforation;

a dilator having a distal end and a proximal end, said dilator configured to pass axially through the lumen of said catheter housing, said dilator having at least one opening in a side wall thereof proximate the distal end of the dilator for permitting passage of the contrast fluid therethrough, said proximal end of said dilator configured to receive said contrast fluid from an external source, said dilator configured with sufficient stiffness to withstand axial forces on said dilator during insertion of the dilator into the lumen of said catheter housing and during insertion of both said dilator and said catheter housing into the patient's vascular system; and an end cap having a central bore therethrough, said end cap configured to seal the proximal end of said catheter housing from fluid flow when said dilator is inserted within the lumen of said catheter housing while said cap is inserted within said proximal end of said catheter housing;

wherein the catheter housing further comprises a distal section, a helical coil positioned within the wall of at least the distal section of said catheter housing for stiffening the catheter housing.

7. A percutaneous catheter assembly comprising:

a catheter housing having a distal end and a proximal end and a lumen therethrough, said distal end configured to penetrate a blood vessel wall and pass axially through the blood vessel without trauma to the patient, said proximal end configured to connect to a standard sized blood pump, said catheter housing having a transition section between the distal end and the proximal end, said catheter housing further comprising a catheter housing side wall having at least one perforation therein in fluid communication with said lumen to permit the passage of a contrast fluid through said perforation;

a dilator having a distal end and a proximal end, said dilator configured to pass axially through the lumen of said catheter housing, said dilator having at least one opening in a side wall thereof proximate the distal end of the dilator for permitting passage of the contrast fluid therethrough, said proximal end of said dilator configured to receive said contrast fluid from an external source, said dilator configured with sufficient stiffness to withstand axial forces on said dilator during insertion of the dilator into the lumen of said catheter housing and during insertion of both said dilator and said catheter housing into the patient's vascular system;

an end cap having a central bore therethrough, said end cap configured to seal the proximal end of said catheter housing from fluid flow when said dilator is inserted within the lumen of said catheter housing while said cap is inserted within said proximal end of said catheter housing; and a disk comprising a synthetic material having a suturing feature, said disk positioned at and surrounding a part of the proximal section of said catheter housing, said disk serving to provide a substrate upon which a treating physician may secure said catheter housing to the patient to minimized relative movement therebetween.

8. A percutaneous catheter assembly for permitting fluid communication with a patient's blood vessel, the assembly comprising:

a catheter housing having a distal end for penetrating the blood vessel and a proximal end for connection to a separate device, said catheter housing comprising a helical coil;

a dilator having a tapered distal end and a proximal end, said dilator configured to pass axially through a lumen of said catheter housing, said proximal end of said dilator configured to receive said contrast fluid from an external source, said dilator having axial struts to provide stiffness;

an end cap configured to seal the proximal end of said catheter housing from fluid flow when said dilator is inserted within the lumen of said catheter housing;

a first set of openings in a side wall of the dilator; and a first set of openings in a side wall of the catheter housing for permitting passage of a contrast fluid through the dilator and the catheter housing into the blood vessel.

9. The assembly of claim 8 wherein the dilator further comprises a second set of openings being distally positioned relative to said first set of dilator openings, said second set of openings being positioned so that at least a part of at least one of such openings in said first set projects distally beyond the distal end of the catheter housing when the dilator is fully inserted within said housing.

10. The assembly of claim 8 wherein the catheter housing further comprises a radiopaque marker.

11. The assembly of claim 8 wherein the helical coil is positioned within the wall of at least the distal section of said catheter housing for stiffening the catheter housing.

12. A method of percutaneous cannulation of a patient's vascular system with a catheter assembly without the need for an introducer sheath or a separate guiding catheter, said method comprising the steps of:

penetrating a blood vessel site with a standard cannulation procedure;

inserting a guide wire into the blood vessel;

placing an end cap within a proximal section of a catheter housing;

placing a dilator through said end cap and within the catheter housing so that a distal tip of the dilator extends beyond a distal tip of the catheter housing, said dilator having means for controlling the flow of contrast therethrough, said catheter assembly comprising the catheter housing, the end cap and the dilator;

placing the catheter assembly over the guide wire and into the blood vessel; and retracting the dilator from the catheter housing and removing the end cap, leaving the catheter housing in place for permitting blood flow therethrough.

13. The method of claim 12 further comprising the steps of:

prior to retraction of the dilator, injecting radiopaque contrast through the dilator and out through a distal end of the dilator to permit detection of the distal end as the catheter assembly is advanced through the patient's vascular system; and, following retraction of the dilator and end cap, attaching a delivery line to a proximal end of the catheter housing for aspiration or infusion.

14. The method of claim 13 wherein the dilator comprises a first set of openings in the side wall thereof, proximate the distal end of the dilator.

15. The method of claim 14 wherein the dilator comprises a second set of openings in the side wall thereof, proximate the said first set of openings.

16. A method of percutaneous cannulation of a patient's vascular system without the need for an introducer sheath or a separate guiding catheter, said method comprising the steps of:

placing an end cap within a proximal section of a catheter housing;

placing a dilator through the end cap and within the catheter housing so that a distal tip of the dilator extends beyond a distal tip of the catheter housing;

placing the catheter assembly over a guide wire within a blood vessel of the patient;

injecting radiopaque contrast through the dilator as the dilator and catheter housing are advanced through the patient's blood vessel; and retracting the dilator from the catheter housing, removing the cap from the catheter housing, and attaching a delivery line to a proximal end of the catheter housing for aspiration or infusion.

17. A method of percutaneous cannulation of a patient's vascular system without the need for an introducer sheath or a separate guiding catheter, said method comprising the steps of:

placing an end cap within a proximal section of a catheter housing;

placing a dilator through the end cap and within the catheter housing so that a distal tip of the dilator extends beyond a distal tip of the catheter housing;

placing the catheter assembly over a guide wire within a blood vessel of patient; and injecting radiopaque contrast through the dilator as the dilator and catheter housing are advanced through the patient's blood vessel;

wherein the dilator comprises a first and second set of openings in the side wall thereof, said first set being positioned proximate the distal tip of said dilator, so that the contrast flows both through the first and second set of openings during the injecting step.

* * * * *

UNITED STATES PATENT AND TRADEMARK OFFICE
CERTIFICATE OF CORRECTION

PATENT NO.   : 6,488,662 B2
DATED        : December 3, 2002
INVENTOR(S)  : Laksen Sirimanne It is certified that error appears in the above-identified patent and that said Letters Patent is hereby corrected as shown below:

Column 11,
Line 44, please delete "lumen of said dilator for stiffening the dilator, the distal end of said dilator having being tapered."

Signed and Sealed this

Seventeenth Day of June, 2003

JAMES E. ROGAN
*Director of the United States Patent and Trademark Office*